(12) United States Patent
Dyshlyuk et al.

(10) Patent No.: US 10,557,783 B2
(45) Date of Patent: Feb. 11, 2020

(54) METHOD FOR DETERMINING EQUILIBRIUM WETTABILITY OF AN INTERFACE BETWEEN A VOID SPACE AND A SOLID PHASE OF A ROCK SAMPLE

(71) Applicant: SCHLUMBERGER TECHNOLOGY CORPORATION, Sugar Land, TX (US)

(72) Inventors: Evgeny Nikolaevich Dyshlyuk, Dhahran (SA); Oleg Yurievich Dinariev, Moscow (RU); Ivan Victorovich Yakimchuk, Moscow (RU); Nikolay Vyacheslavovich Evseev, Moscow (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 105 days.

(21) Appl. No.: 15/562,205

(22) PCT Filed: Mar. 27, 2015

(86) PCT No.: PCT/RU2015/000193
§ 371 (c)(1),
(2) Date: Sep. 27, 2017

(87) PCT Pub. No.: WO2016/159807
PCT Pub. Date: Oct. 6, 2016

(65) Prior Publication Data
US 2018/0120213 A1    May 3, 2018

(51) Int. Cl.
*G06F 11/30*    (2006.01)
*G01N 13/00*    (2006.01)
(Continued)

(52) U.S. Cl.
CPC .......... *G01N 13/00* (2013.01); *G01N 23/046* (2013.01); *G01N 23/05* (2013.01); *G01N 23/207* (2013.01);
(Continued)

(58) Field of Classification Search
CPC ...................................................... G01N 13/00
See application file for complete search history.

(56) References Cited

U.S. PATENT DOCUMENTS 5,162,733 A    11/1992  Baldwin
7,952,698 B2    5/2011  Friedrich et al.
(Continued)

FOREIGN PATENT DOCUMENTS

CN    202854008 U    4/2013
RU    2248561 C1    3/2005
(Continued)

OTHER PUBLICATIONS

Abdallah, W. et al., "Fundamentals of Wettability" Oilfield Review, 2007, 19(2), pp. 44-61.
(Continued)

*Primary Examiner* — Phuong Huynh (57) ABSTRACT

The method for determining equilibrium wettability of an interface between a void space and a solid phase of a rock sample comprises obtaining a three-dimensional image of the internal structure of the sample. On the obtained image of the internal structure of the sample, a void space and a solid phase are differentiated. An interface between the void space and the solid phase of the sample and distribution of minerals on this surface are determined. Wettability of the solid phase at each point of the interface between the void space and the solid phase of the rock sample is determined. A process of oil migration to the void space filled with stratum water at the initial stage of formation of an oil and
(Continued)

gas field is numerically simulated, and finally, the equilibrium wettability of the interface between the void space and the solid phase of the rock sample is determined.

14 Claims, 2 Drawing Sheets

(51) Int. Cl.
  *G01N 23/046* (2018.01)
  *G01N 23/05* (2006.01)
  *G01N 23/207* (2018.01)
  *G06F 17/50* (2006.01)

(52) U.S. Cl.
  CPC ...... *G06F 17/5009* (2013.01); *G06F 2217/16* (2013.01)

(56) References Cited

U.S. PATENT DOCUMENTS

| 9,291,050 B2* | 3/2016 | Seleznev | G01V 3/26 |
| 2012/0011927 A1* | 1/2012 | Badri | G01N 13/00 73/152.05 |
| 2013/0182819 A1 | 7/2013 | Dvorkin et al. | |

FOREIGN PATENT DOCUMENTS

| RU | 2305277 C1 | 8/2007 |
| RU | 2455483 C2 | 7/2012 |
| WO | 2014003596 A1 | 1/2014 |

OTHER PUBLICATIONS

Anderson, W. G., "Wettability Literature Survey—Part 2: Wettability Measurement", Journal of Petroleum Technology, Nov. 1987, 38, pp. 1246-1262.
Anderson, W. G., "Wettability Literature Survey—Part 3: The Effects of Wettability on the Electrical Properties of Porous Media", Journal of Petroleum Technology, Dec., 1986, 38 (12), pp. 1371-1378.
Anderson, W. G., "Wettability Literature Survey—Part 4: Effects of Wettability on Capillary Pressure", Journal of Petroleum Technology, Oct., 1987, 39 (10), pp. 1283-1300.
Anderson, W. G., "Wettability Literature Survey—Part 6: The Efects of Wettability on Waterflooding", Journal of Petroleum Technology, Dec., 1987, 39, pp. 1605-1622.
Anderson, W. G., "Wettability Literature Survey—Part 5: The Effects of Wettability on Relative Permeability", Journal of Petroleum Technology, Nov., 1987, 39 (11), pp. 1453-1468.
Anderson, W. G., "Wettability Literature Survey—Part 1: Rock/Oil/Brine Interactions and the Effects of Core Handling on Wettability", Journal of Petroleum Technology, Oct. 1986, 38 (10), pp. 1125-1144.
Boinovich, L. .et al, "The prediction of wettability of curved surfaces on the basis of the isotherms of the disjoining pressure", Colloids and Surfaces A: Physicochemical and Engineering Aspects, 2011, 383(1-3), pp. 10-16.
Brunauer, S., et al., "Adsorption of Gases in Multimolecular Layers", Journal of the American Chemical Society, 1938. 60 (2), pp. 309-319.
Denoyel, R. et al., "Thermodynamics of wetting: information brought by microcalorimetry", Journal of Petroleum Science and Engineering, 2004, 45(3-4), pp. 203-212.
Donaldson, E.C. et al., "Wettability" Gulf Publishing Company, Houston, Texas, USA, 2008, pp. 2-27.
Mittal, K. L., "Acid-Base Interactions: Relevance to Adhesion Science and Technology", Mittal, Ed., 2000, pp. 317-347.
Morrow, N. R., "Wettability and Its Effect on Oil Recovery", Journal of Petroleum Technology, Dec. 1990, 42 (12), pp. 1476-1484.
Rieger, B. et al., "On Curvature Estimation of ISO Surfaces in 3D Gray-Value Images and the Computation of Shape Descriptors," IEEE Transactions on Pattern Analysis and Machine Intelligence, 2004, 26(8), pp. 1088-1094.
Tabrizy, V. A. et al., "Characterization of Wettability Alteration of Calcite, Quartz and Kaolinite: Surface Energy Analysis", Colloids and Surfaces A: Physicochmical and Engineering Aspects, 2011, 384(1-3), pp. 98-108.
Toponogov, V.A., "Differential Geometry of Curves and Surfaces", Birkhauser, Boston, 2006, pp. 83-86.
Ying, G., "Automated Scanning Electron Microscope Based Mineral Liberation Analysis," Journal of Minerals & Materials Characterization & Engineering, 2003, 2(1), pp. 33-41.

* cited by examiner

METHOD FOR DETERMINING EQUILIBRIUM WETTABILITY OF AN INTERFACE BETWEEN A VOID SPACE AND A SOLID PHASE OF A ROCK SAMPLE

CROSS-REFERENCE TO RELATED APPLICATION

This application is a U.S. National Stage Application under 35 U.S.C. § 371 and claims priority to Patent Cooperation Treaty Application Number PCT/RU2015/000193 filed Mar. 27, 2015, which is incorporated herein by reference in its entirety.

FIELD OF THE INVENTION

The present invention relates to the field of research of interaction between a solid medium and two immiscible liquids, namely, to the study of wetting properties, and is intended to determine the equilibrium wettability of an interface between a void space and a solid phase of a rock sample.

BACKGROUND

Wettability is a surface phenomenon that occurs at a boundary line between phases, one of which is a solid body, and the others are incompatible liquids or liquid and gas. Wettability appears in full or partial spreading of liquid over a solid surface or in bonding to this surface in the presence of another liquid immiscible with the former one. Wettability is an important parameter in many industries, such as pharmaceutical, light industry, oil and gas industry, etc.

For example, in the oil and gas industry, reservoir wettability is one of the key factors for determining a location, flows and distribution of liquids in a reservoir. Being the key factor for determining distribution of liquids in the reservoir, wettability affects many types of geophysical and petrophysical studies of the reservoir—electrical properties, capillary pressure curves, relative permeability, etc. Rock wettability has a significant impact on the choice of optimal oil recovery methods, especially during secondary and tertiary oil production methods.

Wettability is often classified according to the average affinity of liquids to a surface, for example, in the oil and gas industry there are: a water-wetted rock, neutral wettability or an oil-wetted rock; and according to spatial distribution of wettability, for example, in the oil and gas industry: homogeneous, fractional (heterogeneous surfaces with random distribution of rock particles having different wettability), mixed wettability (for example, fine pores are better wetted with water, and coarser pores are better wetted with oil), etc.

Wettability is determined by physicochemical interactions of fluids with each other and with the heterogeneous surface of solid media. Due to complexity of study of surface interactions, up to date there is no universal method for determining wettability. The complex spatial distribution of wettability on the surface of a porous rock is a well-known fact. Determination of the nature of wettability distribution is one of the important tasks in the oil and gas industry.

In most industries the main method used for evaluating wettability is a method of measuring a contact angle between a solid surface and a phase interface of two wetting liquids (see, e.g., W. Abdallah et. al., Fundamentals of Wettability, Oilfield review, vol. 19, no. 2, pp. 44-61, 2007). The disadvantage of this method is the long time required to define an equilibrium wetting angle (up to 1000 h.), the hysteresis of a contact angle conditioned by many reasons such as, but not limited to: a surface structure, surface irregularities, etc. Another disadvantage of the method is that the method is applicable for evaluation of wettability of smooth homogeneous surfaces and it is quite difficult to be realized for characterization of surfaces of porous media and heterogeneous surfaces.

In the oil and gas industry, wettability of a reservoir heavily wetted with water or heavily wetted with oil can be determined, in some cases, by the results of the borehole geophysical research. In most cases, the laboratory research of a rock core is used to study wettability. The USBM methods and the Amott-Harvey method or combinations thereof are considered to be industry-specific standards for evaluating wettability of a core (see, e.g., E. Donaldson and W. Alam, Wettability, Houston: Gulf Publishing Company, 2008, pp. 2-27). Both these methods are based on laboratory simulation of processes of oil displacement with water and water displacement with oil taking place in a stratum. As a result of experiments on determining wettability using these methods, only one number representing wettability: from $-1$ to $+1$ for the Amott-Harvey method and from $-\infty$ to $+\infty$ for the USBM method is found, as a rule, for each core sample. This number does not represent wettability directly, it rather represents the efficiency of displacement of liquids in said processes and, due to the fact that the displacement efficiency depends on wettability, this parameter is related to the state of wettability. At the same time, the resulting number nor allows determining a liquid contact wetting angle on the surface nor gives any information about distribution of wettability on the surface of the core. The complex internal pore structure has an additional effect on the test results regardless of wettability state of the surfaces.

Most of the mentioned methods make it possible to determine the average wettability, while wetting heterogeneity is not evaluable by these methods. As we can ascertain, no method of evaluating spatial heterogeneity of wettability has been nowadays proposed in the oil and gas industry.

SUMMARY OF THE DISCLOSURE

A method according to the present disclosure comprises determining equilibrium wettability of an interface between a void space and a solid phase (mineral matrix, mineral skeleton) of a rock sample in the condition in which the rock is in the stratum after formation of an oil-and-gas field, but before the rock was subjected to man-induced impacts. Namely, it is the influence caused by the impact on the rock by filtrate invasion, mechanical impact on the sample in drilling-out, changes in rock wettability caused by lifting, transportation, storing the corn, etc. Knowing the equilibrium wettability distribution, one can develop a correct model of the reservoir of interest by taking into account the interaction between the solid phase of the rock and fluids saturating the void space. This model is designed to select the optimum mining scenarios of liquid hydrocarbons by their numerical simulation.

The disclosed method for determining the equilibrium wettability of an interface between a void space and a solid phase of a rock sample comprises obtaining a three-dimensional image of the internal structure of the sample. On the obtained image of the internal structure of the sample, a void space and a solid phase are differentiated. An interface between the void space and the solid phase of the sample and distribution of minerals on this surface are determined. Wettability of the solid phase at each point of the interface between the void space and the solid phase of the rock sample is determined. A process of oil migration to the void space filled with stratum water at the initial stage of formation of an oil and gas field is numerically simulated, and finally, the equilibrium wettability of the interface between the void space and the solid phase of the rock sample is determined.

According to one embodiment of the invention, a three-dimensional image of an internal structure of a rock sample is obtained by computed X-ray microtomography, according to other embodiments of the invention—by neutron microtomography or by layer-by-layer electron microscopy using a focused ion beam.

In accordance with one embodiment of the invention, the distribution of minerals on the interface between the void space and the solid phase of the rock sample is determined on the basis of X-ray microtomography data by comparing linear X-ray radiation attenuation coefficients, obtained as a result of scanning the sample, with theoretical linear X-ray radiation attenuation coefficients.

According to another embodiment of the invention, the distribution of minerals on the interface between the void space and the solid phase of the rock sample is determined on the basis of X-ray microtomography data supplemented by the results of energy dispersive X-ray microanalysis.

According to another embodiment of the invention, the distribution of minerals on the interface between the void space and the solid phase of the rock sample is specified according to the volume content of minerals in the sample, determined by applying methods of core analysis, such as X-ray diffraction analysis, section analysis.

In other embodiments of the invention, before determining wettability of the solid phase at each point of the interface between the void space and the solid phase of the sample, a roughness factor of the interface between the void space and the solid phase of the sample is determined, which is taken into account as an effective correction to wettability of the solid phase.

In accordance with one of the embodiments of the invention, the equilibrium wettability of the interface between the void space and the solid phase of the rock is determined by numerical simulation of the process of primary oil migration by individual molecules or clusters of molecules through diffusion inside the stratum water.

According to another embodiment of the invention, the equilibrium wettability of the interface between the void space and the solid phase of the rock is determined by numerical simulation of the process of primary oil migration as a macroscopic phase due to gravity forces (oil density is lower than the stratum water density). In accordance with yet another embodiment of the invention, the joint effect of both migration mechanisms is numerically simulated having a different role at different stages of oil deposit formation.

BRIEF DESCRIPTION OF THE DRAWINGS

The invention is explained in the drawings, in which.

DETAILED DESCRIPTION OF THE DISCLOSURE

According to the modern scientific concept of formation of oil reservoirs, it is believed that initially an interporous space of a porous medium of an oil reservoir is filled with stratum water, therefore, the entire surface of the solid phase of a rock was covered with stratum water. Subsequently, the oil migrated (from the oil-source rock) to the oil stratum region thus displacing the stratum water. After a long (geological) time, the polar components present in the oil could be adsorbed by some parts of the surfaces of the rock solid phase by forming thin films of oil deposits on the surface of the solid phase. As shown by laboratory studies, these deposits are, as a rule, significantly tightly bound to the surface, so that at times these deposits-films can be hardly cleaned off when extracting the corn. In the oil industry, Soxhlet or Dean Stark extraction apparatus are used for cleaning the corn, where strong solvents such as Toluene, Benzene, Methanol, etc. or combinations thereof are circulated through the corn at high temperatures and for a long period of time.

Since the formed adsorbed films of oil components are tightly bound to the surface and will most probably not desorb during development of the field (often not desorbed even with the aforementioned corn cleaning techniques), in order to characterize the rock wettability, it is necessary to determine wettability of the rock coated with films of these deposits, but not directly the wettability of the solid phase of the rock $W^0$ (A). This very state of the rock surface (the thickness of the films of oil deposits is neglected) will be referred to as an equilibrium state. The definition for the equilibrium wettability is assumed to be finding a wettability W(A) parameter for each point of the rock surface A corresponding to the equilibrium state in the stratum.

Figure 1:
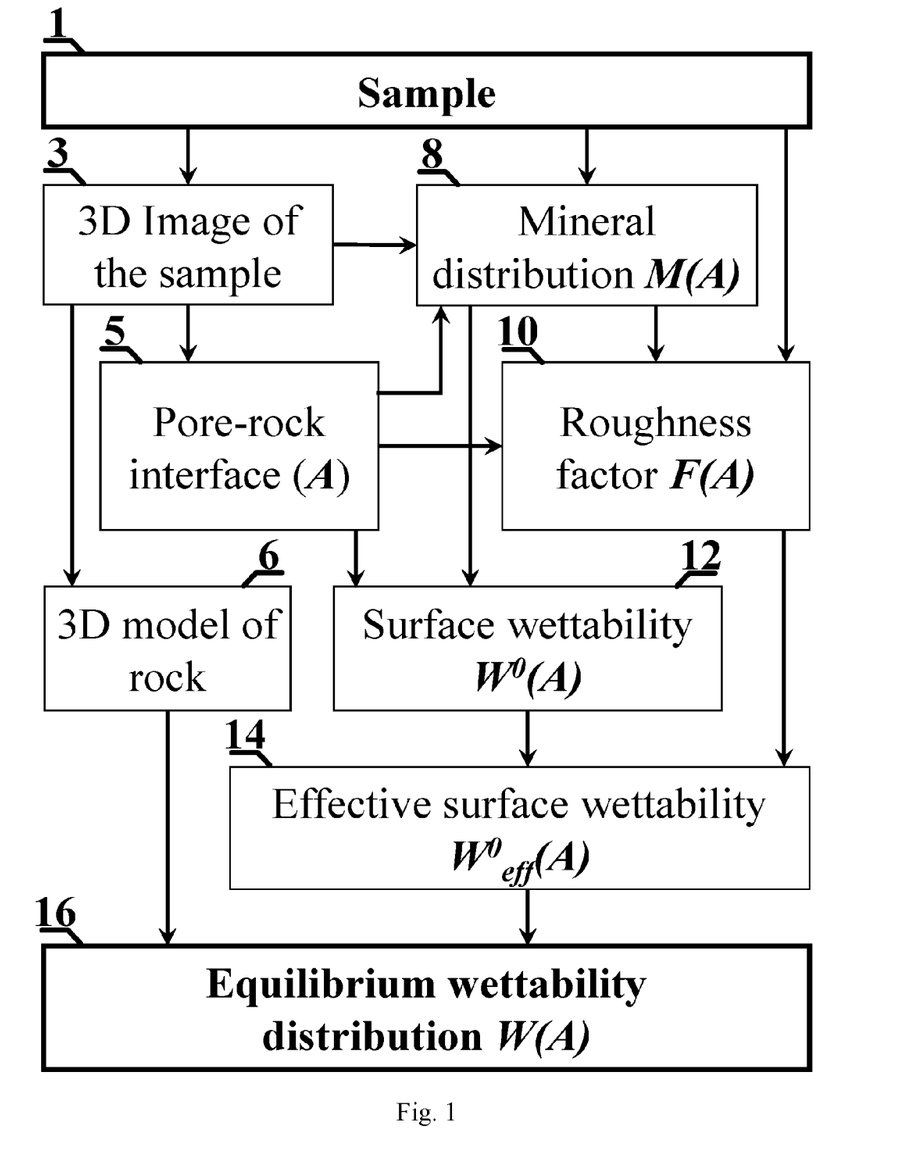
FIG. 1 is a block diagram of an embodiment of the method, where each block corresponds to the results obtained in implementation of the method.
Figure 2:
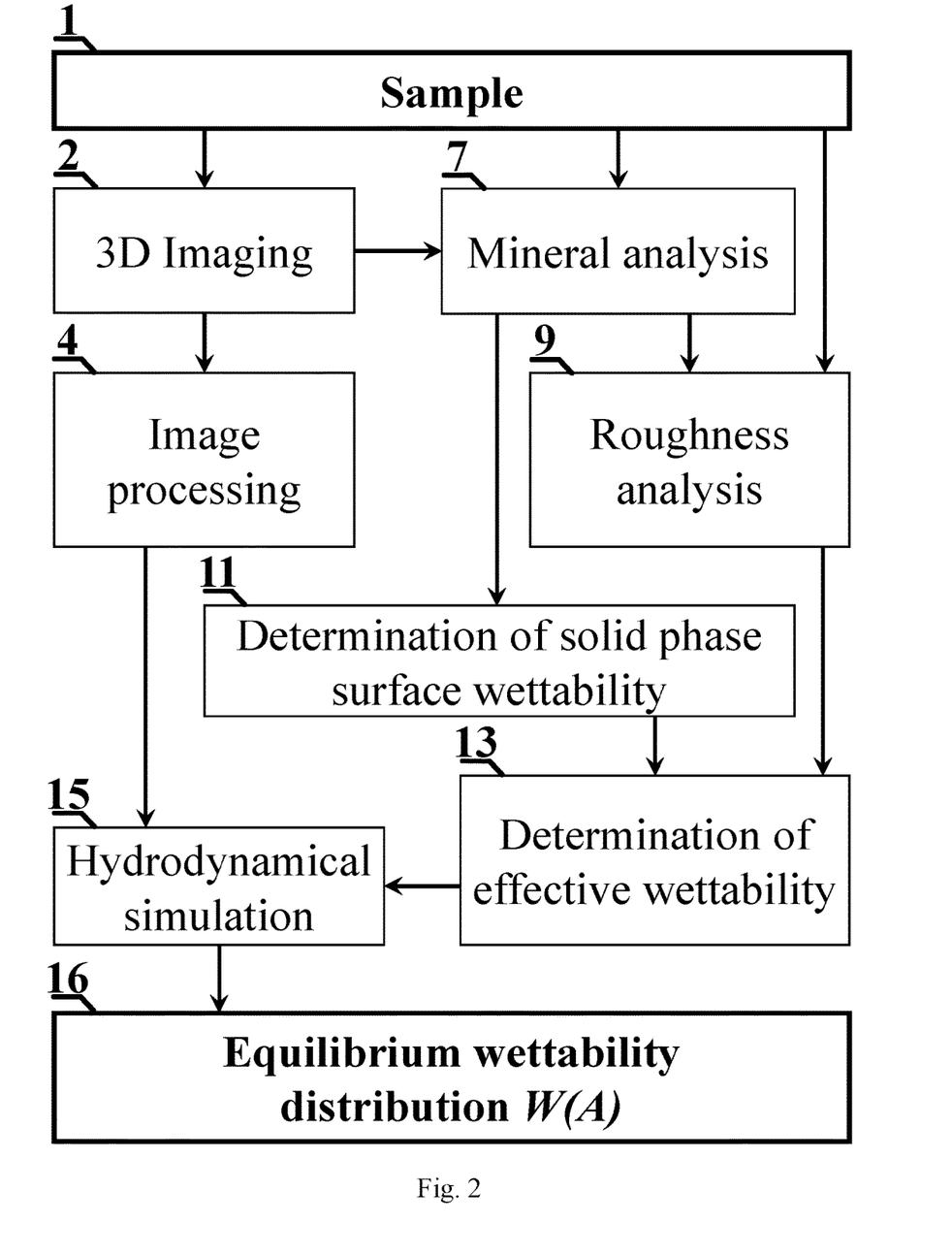
FIG. 2 is a block diagram of the same embodiment of the method but in the form of a flowchart to be fulfilled.

As shown in FIGS. 1 and 2, the disclosed method comprises obtaining an image (scanning) of a rock sample 1 and obtaining 2 a three-dimensional image 3 of the sample 1. Scanning can be performed, for example, by computed X-ray microtomography. The X-ray tomography technique makes it possible to determine spatial distribution of linear attenuation coefficients (LAC) of X-ray radiation inside the sample. In the course of the experiment, the sample of interest is X-rayed from different directions. The transmitted radiation (the shadow projection) is recorded each time by a two-dimensional X-ray detector. Further, the obtained array of shadow projections is reconstructed by any of the known reconstruction algorithms (for example, back projection, algebraic approach). The reconstructed data is a layered representation of the internal structure of the sample.

Scanning can also be performed using neutron microtomography. The principal difference between this technology and the X-ray tomography is probing a sample with a beam of neutrons, rather than with X-ray photons. All other key elements of the microtomographic experiment remain practically unchanged. As a result of reconstruction, a three-dimensional image of neutron beam attenuation coefficients is formed. Thus, the contrast observed on the image has a nature other than the X-ray contrast. In this case, as with the X-ray, the contrast between the solid phase and the pores is sufficient for segmentation.

It is also possible to use other techniques of obtaining three-dimensional images, including higher resolution images. Examples of such techniques can be X-ray nanotomography, raster (scanning) electron microscopy with a built-in system of focused ion beam etching of a sample. The latter technology allows etching away layer upon layer a small sub-region of a sample in increments of 10 nm. Subsequent to etching, these layers are exposed to a scanning electron beam. As a result, a three-dimensional image of a near-surface volume of about 10×10×10 μm and a resolution of about 10 nm is formed. A combination of the above techniques is also possible.

Then, the processing 4 procedure of the obtained image 3 of the sample 1 is carried out, which consists in allocating a void space and a solid phase and in determining the (pore-rock) interface 5 between the void space and the solid phase of the sample.

The three-dimensional image with marked voids and a solid phase represents a model 6 of a void space of a rock sample, on which oil migration in the stratum will be ultimately calculated 15.

For further implementation of the invention, it is convenient to use an oriented surface as the surface 5. Hereinafter, an oriented surface is referred to as the presence of a consistently defined parameter at each point thereof, which determines from which side of its boundary there is a solid phase, and from which side there is a pore, that is, a void space. Such parameter can be a normal to the surface everywhere directed from the rock to the pore (or vice versa).

Suppose A is the oriented interface between the void space and the solid phase of the rock sample of interest with the normal directed from the rock to the pore. In general, any of the known coordinate systems of a three-dimensional space (for example, a rectangular Cartesian (x, y, z) system) can be used to describe the surface A. To determine the A from the obtained three-dimensional image of the internal structure of the porous rock sample, expressed in the attenuation coefficient values, it is necessary to perform the following operations: segmentation of a three-dimensional image (binarization); selection of points of the three-dimensional image (voxels) corresponding to the boundaries of the pore-rock interface; determining the normals to the surface in each voxel.

To build up a model 6 of a void space, i.e. to differentiate a void space and a solid phase on the obtained three-dimensional image, it is necessary to perform only segmentation of the three-dimensional image (binarization). The procedures of segmentation, necessary for building up the void space model 6, and determination of the interface 5 between the void space and the solid phase are absolutely identical.

Segmentation of a three-dimensional image can be carried out by any of the known techniques most suitable in each particular case, depending on data quality and the structure of the object of interest. One of possible variants is disclosed in application WO/2014/003596. As a result, a three-dimensional array (a set of two-dimensional images) must be obtained, in which, in case of binarization, the value "0" corresponds to a pore space, and the value "1" corresponds to a rock. Instead of "1" any other predefined number can be taken. For example, the value "255" is often used for 8-bit images. Without restricting the generality, hereinafter the use is made of the value "1".

The selection of boundary voxels is necessary for creation of a discrete representation of the desired surface 5. This operation can be performed by several methods. For example, during segmentation, voxels that had close probabilities of belonging to both classes (pore "0" and rock "1") can be classified as boundary ones. Another possibility is to determine the boundary by the known "erosion" morphological technology. The essence of the operation consists in that all voxels with value "1", spaced from any of the voxels with value "0" by a distance less than the predefined d, are assigned the value "0". Further, the obtained array can be elementwise subtracted from the original segmented one. As a result, an array with the value "1" will be obtained at the voxels belonging to the pore-rock boundary having thickness d. It seems optimal to use d=1. In the described embodiment, the original non-segmented images are not required.

The normals to the surface in each voxel can be determined by various methods. For example, orientation of the surface at each point of the boundary found at the previous step can be determined by calculating a gradient vector of the reconstructed microtomographic image at the same point. This approach is based on the fact that the void space (filled with air or other gas, water or hydrocarbons, etc.) has a lower LAC value as compared with the solid (mineral) phase. For this reason, at the pore-rock boundary, the LAC field gradient is directed perpendicular to the boundary from smaller values in the pore to larger values in the solid phase. The gradient vector is recommended to be calculated in a small neighborhood of the selected point to abate the noises on the reconstructed sample images. The size of the neighborhood is determined by both the imaging structure (characteristic dimensions of the features) and the noise characteristics.

Mineral analysis 7 is then carried out, i.e. the distribution of 8 minerals on the interface 5 between the void space and the solid phase of the sample is determined. Different minerals have different wettability properties. For this reason, determination of wettability properties of the surface of a void space requires consideration of its mineral composition. Let's denote by M(A) the correspondence between points on the surface A and their mineral composition M in a small neighborhood of each point. Thus, the values of M must uniquely indicate the type of a mineral of the corresponding point. Technically, it is convenient to realize it in the form of a table of integer numbers, each encoding one or another type of mineral. These numbers are then assigned to all points of the surface A depending on their mineral identity. In the simplest case of a monomineral surface, the M(A)=M, where M corresponds, for example, to quartz, dolomite, etc. In more complex cases, it becomes necessary to determine the M(A), which can be accomplished by various methods. It is apparent that due to the limited spatial resolution of the resulting three-dimensional image, at one point (voxel) of the surface A there may be several minerals (a mixture of minerals). In this case, it seems expedient to single out such mixtures into separate conditional types of minerals and to carry out all further procedures for them as for independent minerals. If the number of such points on the surface A is insignificant, then introduction of additional conditional minerals corresponding to the mixtures of actual minerals does not make sense and only complicates implementation of the invention.

The distribution of M(A) can be determined directly basing on X-ray m crotomography data, namely, from the reconstructed LAC values and their comparison with the theoretical ones. The LAC value for each substance (in particular, a mineral) depends on its chemical composition, mass density and energy of the probing X-ray beam. In case with the known energy spectrum of the beam, the mineral type at a point can be approximately determined by correlating the reconstructed and theoretically calculated LAC values (see, for example, J. H. Hubbel and S. S. M., "NIST X-ray Attenuation Databases," The National Institute of Standards and Technology NIST), [Online]. Available: http://www.nist.gov/pml/data/xraycoef/index.cfm.). Some minerals have too close LAC values and are usually indistinguishable.

It is possible to determine the M(A) based on X-ray microtomography data, supplemented by the results of energy-dispersive X-ray microanalysis of any region (cross-section) of the sample of interest (Energy Dispersive X-Ray microanalysis, EDX) performed in scanning electron microscopy systems (Scanning Electron Microscopy, SEM (see, for example, G. Ying, "Automated Scanning Electron Microscope Based Mineral Liberation Analysis," Journal of Minerals & Materials Characterization & Engineering, vol. 2, no. 1, pp. 33-41, 2003). In the EDX-SEM method, the characteristic X-ray spectrum (excited by an electron beam of a microscope) is recorded at each point of the scanned surface of the sample. For the best result, it is recommended to prepare a flat surface on specialized machines in accordance with the requirements of the EDX-SEM method (pouring of the original sample with epoxy resin, cutting where desired, dressing, polishing and deposition of the conductive material). The obtained spectra can be interpreted and presented in the form of a quantitative chemical composition. To further determine the distribution of minerals on the scanned surface, it is necessary to use a library of mineral spectra, need to be created independently. Another possibility consists in using commercially available software for mineral identification. Although this is only information about a surface (or a cross-section), the resulting mineral distribution can be representative in order to expand distribution to a three-dimensional microtomography image and/or directly to A (for example, basing on the reconstructed LAC values with preliminary spatial superimposition of mineral distribution and 3D microtomography image).

The volume content of minerals in the rock can be known from the results of study of the core (for example, using X-ray diffraction technologies). In this case, distribution of minerals M(A) on the internal surface of the digital model of the sample can be made in accordance with the volume content. This procedure can be carried out either randomly with a defined probability distribution of the presence of minerals, or using a more complex method by taking into account the general knowledge about the structure, architecture and distribution of definite minerals in a definite rock. Thus, for a fragmental rock having a defined volume content of quartz of 95% and clays of 5%, it is worthwhile distributing the clays on the surface near the junctions of grains, and quartz—on the surface of the grains themselves away from the junctions.

There are also other techniques that can be used to determine the volume content of minerals and, in particular their distribution 8 on the surface M(A). Such techniques may include, for example: synchrotron microtomography using monochromatic X-ray radiation, X-ray fluorescence microtomography, X-ray topo-tomography.

In addition to distribution of minerals, topographic features of the surface can be taken into account for more correct determination of wettability properties on the sample surface. These features can be taken into account through the procedure 9 of determining the parameters of the local surface roughness. In general, the surface roughness must be described by a whole set of parameters. Among them, the most important for determining wettability is a roughness factor 10, which is calculated on the surface A:

$$F(A) = \frac{S_{True}(A) - S_{CT}(A)}{S_{CT}(A)} \cdot 100\%, \quad (1)$$

where $S_{True}(A)$ is the actual area of the pore-rock interface in some small neighborhood of the point of interest, and $S_{CT}$ is the area of the surface A constructed based on microtomography data and computed in the same neighborhood of the same point. The roughness factor (1) reflects the difference in surface areas calculated at A and using other higher resolution techniques.

The procedure 9 for estimating the values 10 of the parameter F(A) at each point of the surface A can be performed by different methods. For example, direct measurements are possible using any available surface topography technique for each mineral contained in the sample. Further, a roughness factor for each of them F(M) is calculated. Finally, considering the previously determined distribution M(A), it is easy to calculate F(A).

The roughness factor for a particular mineral can be approximately estimated on the basis of literature data. For previously determined interface A between the void space and the solid phase of the porous sample of interest, it is easy to calculate the total area (the surface area of the sample, including the void space). The area calculated this way can be compared with the similar value measured laboratorially for the same (preferably) or similar sample. The surface area of a rock sample can be measured, for example, by the widely known BET method (see, for example, S. Brunauer, P. Emmett and E. Teller, "Adsorption of Gases in Multimolecular Layers," J. Am., Chem. Soc., Vol. 60, p. 309, 1938) or any other. Further, the roughness factor is selected such that the found areas satisfy (1).

The use of higher resolution imaging techniques provides for direct reconstruction, visualization and quantification of true surface topography. Examples of such techniques may be X-ray nanotomography, raster (scanning) electron microscopy, including with a built-in sample etching system by a focused ion beam. The latter technology allows etching away layer upon layer a small sub-region of a sample in increments of 10 nm. Subsequent to etching, these layers are exposed to a scanning electron beam. As a result, a three-dimensional image of a near-surface volume of about 10×10×10 μm and a resolution of about 10 nm is formed. A combination of the above techniques is also possible.

Then, wettability of the solid phase is determined 11 at each point of the sample, by taking into account the obtained surface distribution of minerals M(A) and a roughness factor F(A). Determination 11 of wettability 12 of the solid phase of the rock $W^0(A)$ means that each point of the surface A has the assigned value:

$$W^0(A) = \frac{\gamma^{SO}(A) - \gamma^{SW}(A)}{\gamma^{OW}}, \quad (2)$$

where the indices S (solid), O (oil), W (water) denote a rock surface, oil and water respectively, $\gamma^{XY}$ is the surface tension at a boundary between the phases X and Y.

To determine the $W^0(A)$, several methods can be used.

It is possible to measure wettability W(M) of the surfaces of minerals M, that constitute the surface of interest, with oil and stratum water. Wettability of each mineral can be measured separately using the methods for measuring a contact angle, calorimetry, gas adsorption or any other known method for measuring wettability. Further, knowing the distribution of minerals M(A) on the surface A, it is easy to determine $W^0(A)$.

In case where isolation of each mineral for investigating its wettability properties by said oil and water is not possible or is associated with significant difficulties, the following variant of determining the $W^0(A)$ is possible. Wettability of minerals that constitute the surface is determined by the surface tension component theory. Literature data can be used to determine the surface tension components of the solid surface of each mineral, for example, K. Mittal, Acid-Base Interactions: Relevance to Adhesion Science and Technology, Mittal, Ed., 2000, pp. 317-347, and in order to determine the surface tension component constituents of oil and water to be studied, experimental measurements of the component constituents could be used by implementing the three liquids approach and interfacial tension measurements according to sitting, hanging or spinning drop technique or any other known technique for measuring liquid—liquid surface tensions. Further, as mentioned above, knowing the distribution of minerals M(A) on the surface A, it is easy to determine $W^0(A)$.

In case where similar studies of interfacial tensions of liquids are not possible, the wettability of each mineral is evaluated based on available literature data on wettability of minerals with the mineral solution and oil having closest properties. Further, knowing the distribution of minerals M(A) on the surface A, one can determine $W^0(A)$.

As it was mentioned above, determination of the equilibrium wettability 16 is referred to as finding a wettability parameter W(A), for each point of the surface A of the rock, corresponding to the equilibrium state in the stratum, after oil and gas field formation. For this reason, it is further proposed to perform hydrodynamic simulation 15, namely, to simulate the process of oil migration to the void space of the rock, filled with stratum water at the initial stage of the field formation, in accordance with our knowledge and/or assumptions about the history of this process in this stratum. During simulation the system comes in an equilibrium state. Based on the obtained equilibrium distribution of fluids (oil, stratum water) the total distribution 16 of the wettability parameter W(A) is determined. As it will be shown below, this simulation is performed on the constructed model 6 using the found distributions of wettability 12 and a roughness factor 10.

In the scientific environment, there are two main scenarios for formation of the equilibrium state in a stratum. It is assumed that before the oil and gas field formation the stratum was filled with stratum water. In the process of oil migration to the stratum, oil migrates either by individual molecules or by clusters of molecules through diffusion inside the stratum water, or as a macroscopic oil phase (drops or continuous channels wetted with oil connecting an oil source rock and a reservoir) due to gravity forces (oil density is lower than the stratum water density). Of course, there is a probability of joint effect of the above migration mechanisms having a different role at different stages of the oil deposit formation.

Simulation of both scenarios of oil migration can be carried out by different methods. For example, by calculating the distribution of liquids in the space of a porous medium basing on minimization of the total Helmholtz free energy. Similar calculations can be performed using the density functional method in hydrodynamics (A. Y. Demianov, O. Y. Dinariev and N. V. Evseev, Introduction to the density functional method in hydrodynamics, Moscow: Fizmatlit, 2014, pp. 37-70). This method allows simulating hydrodynamic and diffusion processes in multicomponent liquids occurring in complex three-dimensional geometries.

In the event that oil migrates into the oil stratum as separate molecules, the equilibrium state of wettability of the rock W(A) can be determined if the saturation of the sample of interest with oil $S_O$ (the ratio of the volume of the porous space occupied by oil to the total volume of the porous sample of the space), wettability 12 of the solid phase of the rock $W^0(A)$, a roughness factor 10 of the surface F(A), and a model of the void space 6 are specified.

The saturation $S_O$ is specified based on information about the stratum of interest. This value imposes a condition on the initial distribution of oil and stratum water in the mixture filling the void space of the sample. One of the possible variants of the initial conditions for distribution of liquids can be uniform distribution of the components (oil, stratum water) inside the pores of the rock in the proportion corresponding to the required oil saturation $S_O$.

Wettability of the rock solid phase together with the roughness factor of the surface F(A) define the effective initial wettability 14 ($W_{eff}^0(A)$) at the points of the surface A, which is then explicitly used in numerical simulation 15 of the system hydrodynamics. The procedure 13 of defining the $W_{eff}^0(A)$ through $W^0(A)$ and F(A) can be carried out by different methods, for example, according to (3).

$$W_{eff}^0(A)=W^0(A)\cdot F(A), \quad (3)$$

As a result of calculations using this method, the system comes to an equilibrium state corresponding to a minimum of Helmholtz total free energy. For example, in case of a homogeneous distribution of wettability of the solid phase on the surface, $W_{eff}^0(A)=W_{eff}^0=$const, depending on the value $W_{eff}^0$ the following four variants of the equilibrium distribution of liquids are possible (A. Y. Demianov, O. Y. Dinariev and N. V. Evseev, Introduction to the density functional method in hydrodynamics, Moscow: Fizmatlit, 2014, pp. 57-70, 76-86):

$W_{eff}^0<-1$: The entire surface of the rock is covered with a layer of water, the oil occupies the central part of the pores, without contact to the surface of the rock.

$-1<W_{eff}^0<0$: Water occupies all pores with a large area/volume ratio (AV is the ratio of the surface area of a given pore to its volume). Whereas oil will occupy the pores having a minimum AV ratio. Equilibrium distributions will be determined by fluid saturations.

$0<W_{eff}^0<1$: On the contrary, oil will occupy all pores with a larger AV ratio, and water—with a smaller AV ratio.

$W_{eff}^0>1$: The entire surface of the rock will be covered with a layer of oil. Water will occupy the central part of the pores, without contact to the surface.

To determine the equilibrium distribution of wettability of the entire surface A, it is further assumed that after the system comes to the equilibrium state, those surfaces of the solid phase that have appeared in the equilibrium state in contact with oil ($A_O$) have changed the wettability, while the wettability of the remaining part of the surface ($A_W$, covered with water)—is left unchanged. To specify the changed wettability of the surface $A_O$, various methods can be used, for example, the wettability of the formed oil deposits in the water-oil-film system can be studied separately. In the simplest case, one can assume that $W(A_O)=-1$. Thus, in this case, the equilibrium wettability of the rock will be determined by the wettability of the solid phase W (Aw)=$W_{eff}^0$ (Aw) of that part of the surface that came in contact only with water (upon the results of equilibrium distribution), the wettability of the remaining part of the sample surface is assumed as $W(A_O)=-1$.

In case of the scenario of oil movement as a macroscopic phase, it is believed that oil migrates to the rock as a macroscopic phase. By displacing stratum water from the pore space, the oil can come in contact with the surface, resulting in formation of an adsorbed film of polar oil components on the surface that can change wettability of the rock.

Let's consider a thin film of stratum water between the rock surface and the oil phase. Gravity forces and capillary pressure push oil towards the solid surface, while the resulting disjoining pressure in the film either counteracts these forces (in case of a positive disjoining pressure) or vice versa, contributes to these forces by reducing the film thickness (negative disjoining pressure).

For complex geometry of the rock surface, when considering the balance of forces, it is also necessary to take into account the additional Laplace pressure occurring due to curvature of the film surface near the rock surface:

$$\Delta P_{Laplace} = \gamma^{ow}\left(\frac{1}{R_1} + \frac{1}{R_2}\right) = \frac{\gamma^{ow}}{R}, \quad (4)$$

where $R_1$ and $R_2$ are the main radii of the curvature of the oil-water phase interface, and $R=R_1 R_2/(R_1+R_2)$ is the effective local curvature of the surface. Hereinafter, in spite of the fact that the local curvature of this surface may differ slightly from the local curvature of the solid surface near which this film is located, we will assume that this difference is insignificant, taking them equal to each other. Taking into account the fact that the thickness of thin films is units—hundreds of nanometers, this assumption seems justified in describing this method.

Thus, as the oil approaches the curved surface of the rock, the Laplace pressure will either tend to reduce the thickness of the thin water film (with a convex surface) or to increase the thickness of the thin film (with a concave surface). Consequently, the probability that oil will directly come in contact with the surface is higher for convex surfaces and lower for concave surfaces, wherein this probability will be controlled by the effective curvature of the surface at a given point.

To determine the local effective curvature of the surface at each point of the surface A several methods can be used. For example, it is possible to determine using the direct method from the discrete surface representation in step 2 with subsequent calculation of the required derived coordinate values (V.A. Toponogov, Differential Geometry of Curves and Surfaces, Birkhauser, Boston, 2006, pp. 83-86).

The curvature can also be calculated on the original 3D image (see, for example, B. Rieger, F. J. Timmermans, L. J. van Vliet and P. W. Verbeek, "On Curvature Estimation of ISO Surfaces in 3D Gray-Value Images and the Computation of Shape Descriptors," IEEE Transactions on Pattern Aanalysis and Machine Inteliigence, vol. 26, no. 8, pp. 1088-1094, 2004). In this case, at each point of the three-dimensional image, structural gradient intensity tensors are calculated, for which the problem of searching for proper vectors and proper values is then solved. For voxels lying on the pore-rock interface, the proper vector with a larger proper value corresponds to the normal to this surface, while the other two correspond to the two main directions of the curvatures of the surface at a given point in the three-dimensional space. The norms of the vectors derivative of the vector field of normals along these two directions at each point of the pore-rock surface (surface A) define a pair of values $R_1$ and $R_2$ of the main curvatures of the surface at the point of interest.

Other methods of determining the local effective curvature of the surface at each point of the surface A are also possible.

In the mentioned above methods it is expedient to carry out calculations in a small neighborhood of the point of interest to suppress the noise effect artifacts on the image as well as data discreteness.

After the effective curvature of the surface is found, the Laplace pressure (4) can be calculated. Further, if the isotherms of the disjoining pressure (from literature data or measured) of a thin water film, formed between the surface of a given mineral and oil, are known, the equilibrium thickness of the water film can be calculated (see, for example, L. Boinovich and A. Emelyanenko, "The prediction of wettability of curved surfaces on the basis of the isotherms of the disjoining pressure, "Colloids and Surfaces A: Physicochemical and Engineering Aspects, vol. 383, pp. 10-16, 2011). Thus, it is possible to determine in which regions of the surface there is no water film (the film thickness is equal to zero) and, consequently, the polar components of oil could change the wettability of the given region of the surface. The wettability of this part of the surface changes by $W(A_O)=-1$, and the wettability of the remaining part of the surface remains unchanged.

If the disjoining pressure isotherm is not known, then for determining the wettability, which has changed wettability, it is necessary to select a curvature of the surface—the critical value R'. A surface having curvature greater than this value R', according to this assumption, has changed the wettability due to adsorption of the polar oil components on a given part of the surface, while the surface having less curvature of the surface has not changed the wettability.

Several options can be used to select the critical value R'. With the known ratio of the surface areas coated with adsorbed oil components to the total surface area—the hydrophobic coefficient—the value R' can be selected iteratively by calculating the surface area corresponding to the surface having curvature smaller than R' and larger than R'. If the ratio of the areas of these surfaces is unknown, then the critical value R' can be selected iteratively by the following procedure. Any value, for example, R'=0, can be taken as an initial value R'. For the entire surface having smaller curvature, the wetting conditions do not change and for the surface having larger curvature, the wetting conditions change by W=-1. Further, using computer simulation, for example, by the density functional method, the parameters depending on wettability can be calculated, such as, for example, relative phase permeabilities, electrical conductivity, etc. As a result of the simulation, the parameter R' is selected, which makes it possible to approximate simulating results to the similar experimental results in the best way.

After the critical value of the surface curvature is determined, the equilibrium wettability of the surface is determined as follows: wettability of a surface having local curvature less than the critical value remains unchanged (equal to wettability of the solid phase of the rock $W^0$), and wettability of the rest part of the surface changes by $W(A_O)=-1$.

The basic procedures of the described method (obtaining an image 2, performing segmentation 4, determining the distribution of minerals 7, accounting for the roughness factor 9 and, of course, the simulation of the primary oil migration process 15) are realized using electronic computer systems. This system can be the only one for all the above procedures. However, as a rule, different computers are used for each of the tasks. The general requirements for all these computing systems consist in the presence of:

a processor to perform the necessary commands and calculations;

a memory for storing temporary and permanent information (with a volume sufficient for operation with the received data);

input and output devices for management and control of the performed procedures;

as well as the possibility of information transfer through a network or removable media.

In the simplest case of implementation of the invention, such a computing system can be a personal computer.

The invention claimed is:

1. A method for determining equilibrium wettability of an interface of a void space and a solid phase of a rock sample, the method comprising:
    obtaining a three-dimensional image of an internal structure of a rock sample,
    on the obtained three-dimensional image of the internal structure of the sample, differentiating a void space and a solid phase, and determining an interface of the void space and the solid phase of the sample,
    determining distribution of minerals on the interface between the void space and the solid phase of the sample,
    determining wettability of the solid phase at each point of the interface between the void space and the solid phase of the rock sample,
    numerically simulating the process of oil migration in the void space of the sample and
    determining the equilibrium wettability of the interface between the void space and the solid phase of the rock sample.

2. The method according to claim 1, wherein obtaining of the three-dimensional image of the internal structure of the rock sample is performed by computer X-ray microtomography.

3. The method according to claim 1, wherein obtaining of the three-dimensional image of the internal structure of the rock sample is performed by neutron microtomography.

4. The method according to claim 1, wherein obtaining of the three-dimensional image of the internal structure of the rock sample is performed by layer-by-layer electron microscopy using a focused ion beam.

5. The method according to claim 2, wherein the distribution of minerals on the interface between the void space and the solid phase of the sample is determined basing on X-ray microtomography data by comparing linear X-ray radiation attenuation coefficients, obtained as a result of scanning the sample, with the theoretical linear X-ray radiation attenuation coefficients.

6. The method according to claim 3, wherein the distribution of minerals on the interface between the void space and the solid phase of the sample is determined basing on neutron microtomography data by comparing neutron beam attenuation coefficients, obtained as a result of scanning the sample, with the theoretical ones.

7. The method according to claim 5, wherein the distribution of minerals on the interface between the void space and the solid phase of the sample is determined basing on X-ray microtomography data, supplemented by the results of energy dispersive X-ray microanalysis.

8. The method according to claim 1, wherein the distribution of minerals on the interface between the void space and the solid phase of the sample is specified according to the volume content of minerals in the sample, determined by applying a method of core analysis.

9. The method according to claim 8, wherein X-ray diffraction analysis is applied as the method of core analysis for determining the volume content of minerals in the sample.

10. The method according to claim 8, wherein section analysis is applied as the method of core analysis for determining the volume content of minerals in the sample.

11. The method according to claim 1, wherein before determining wettability of the solid phase at each point of the interface between the void space and the solid phase of the sample, a roughness factor of the interface is determined, which is taken into account as an effective correction to the wettability of the solid phase.

12. The method according to claim 1, wherein the equilibrium wettability of the interface between the void space and the solid phase of the rock is determined by numerical simulation of the process of primary oil migration by individual molecules or by clusters of molecules through diffusion within the stratum water.

13. The method according to claim 1, wherein the equilibrium wettability of the interface between the void space and the solid phase of the rock is determined by numerical simulation of the process of primary oil migration as a macroscopic phase due to gravity forces.

14. The method according to claim 1, wherein the equilibrium wettability of the interface between the void space and the solid phase of the rock is determined by numerical simulation of the process of primary oil migration simultaneously by individual molecules or by clusters of molecules through diffusion within the stratum water, and by a macroscopic oil phase due to gravity forces.

* * * * *